United States Patent [19]

Peck et al.

[11] Patent Number: 5,762,645

[45] Date of Patent: Jun. 9, 1998

[54] FASTENING DEVICE AND METHOD OF USE

[75] Inventors: Daniel Charles Peck; Patrick Jay Allen, both of Cincinnati, Ohio

[73] Assignee: The Procter & Gamble Company, Cincinnati, Ohio

[21] Appl. No.: 710,038

[22] Filed: Sep. 11, 1996

Related U.S. Application Data

[63] Continuation-in-part of Ser. No. 547,847, Oct. 25, 1995, Pat. No. 5,647,864, which is a continuation of Ser. No. 254,814, Jun. 6, 1994, abandoned.

[51] Int. Cl.$^6$ .................................................. A61F 13/15
[52] U.S. Cl. ........................ 604/391; 24/304; 24/306; 24/442; 24/DIG. 11
[58] Field of Search ............................ 604/391; 24/304, 24/306, DIG. 11, 442–452

[56] References Cited

U.S. PATENT DOCUMENTS

| | | |
|---|---|---|
| 2,039,312 | 5/1936 | Goldman . |
| 2,397,838 | 4/1946 | Chavannes . |
| 3,094,330 | 6/1963 | Smith ........................... 273/54 |
| 3,176,364 | 4/1965 | Dritz . |
| 3,206,343 | 9/1965 | McFarlane ..................... 156/72 |
| 3,214,323 | 10/1965 | Russell et al. . |
| 3,266,841 | 8/1966 | Altman . |
| 3,277,547 | 10/1966 | Billarant . |
| 3,319,307 | 5/1967 | Marforio . |
| 3,327,708 | 6/1967 | Sokolowski . |
| 3,405,430 | 10/1968 | Sidelman . |
| 3,469,289 | 9/1969 | Whitacre . |
| 3,490,107 | 1/1970 | Brumlik . |
| 3,494,006 | 2/1970 | Brumlik . |
| 3,527,629 | 9/1970 | Wylde ........................... 156/72 |
| 3,665,921 | 5/1972 | Stumpf . |
| 3,665,922 | 5/1972 | Skora . |
| 3,694,867 | 10/1972 | Stumpf . |
| 3,708,833 | 1/1973 | Ribich et al. . |
| 3,895,797 | 7/1975 | Moore .......................... 273/32 A |
| 3,949,128 | 4/1976 | Ostermeier .................... 428/152 |
| 4,116,892 | 9/1978 | Schwarz ....................... 521/62 |
| 4,169,303 | 10/1979 | Lemelson . |
| 4,223,059 | 9/1980 | Schwarz ....................... 428/198 |
| 4,239,829 | 12/1980 | Cohen ........................... 24/DIG. 11 |
| 4,355,066 | 10/1982 | Newman ....................... 428/198 |

(List continued on next page.)

FOREIGN PATENT DOCUMENTS

| | | |
|---|---|---|
| 0 217 032 A3 | 4/1987 | European Pat. Off. . |
| 0 258 015 | 3/1988 | European Pat. Off. . |
| 0 341 993 | 11/1989 | European Pat. Off. . |
| 0 393 953 | 10/1990 | European Pat. Off. . |
| 0 418 951 A2 | 3/1991 | European Pat. Off. . |
| 0 604 731 A1 | 7/1994 | European Pat. Off. . |
| 0 672 516 A2 | 9/1995 | European Pat. Off. . |
| 1140576 | 1/1969 | United Kingdom . |
| 1299897 | 12/1972 | United Kingdom . |
| 2 285 093 | 6/1995 | United Kingdom . |
| WO 92/01401 | 2/1992 | WIPO . |
| WO 94/08789 | 4/1994 | WIPO . |
| WO 95/04654 | 2/1995 | WIPO . |
| WO 96/25905 | 8/1996 | WIPO . |

*Primary Examiner*—Mary Beth Jones
*Attorney, Agent, or Firm*—David M. Weirich; Steven W. Miller; Jacobus C. Rasser

[57] ABSTRACT

A fastening system including a male component and a female component. The male component includes a base having a first fastening surface and an opposed first nonfastening surface. The first fastening surface has a plurality of engaging elements extending, each engaging element having a proximal end adjacent the first fastening surface, a stem extending outwardly from the proximal end and distal end spaced apart from the proximal end by the stem. The female component includes a backing having a second fastening surface and an opposed second nonfastening surface; and a receiving material joined to said second fastening surface. At least a portion of the second fastening surface includes a bonding element such that when the fastening system is in a closed, fastened configuration, at least a portion of the distal end of some of the engaging elements of the male component pass through the receiving material and are joined to the second fastening surface with the bonding element.

20 Claims, 3 Drawing Sheets

U.S. PATENT DOCUMENTS

| | | | |
|---|---|---|---|
| 4,374,888 | 2/1983 | Bornslaeger | 428/198 |
| 4,379,192 | 4/1983 | Wahlquist et al. | 428/156 |
| 4,418,123 | 11/1983 | Bunnelle et al. | 428/517 |
| 4,600,618 | 7/1986 | Raychok, Jr. et al. | 428/92 |
| 4,725,473 | 2/1988 | Van Gompel et al. | 428/156 |
| 4,761,318 | 8/1988 | Ott et al. | 428/85 |
| 4,761,322 | 8/1988 | Raley | 428/198 |
| 4,891,258 | 1/1990 | Fahrenkrug | 428/138 |
| 4,943,340 | 7/1990 | Ujimoto et al. | 156/496 |
| 4,973,326 | 11/1990 | Wood et al. | 604/391 |
| 5,032,122 | 7/1991 | Noel et al. | 604/391 |
| 5,043,036 | 8/1991 | Swenson | 156/160 |
| 5,058,247 | 10/1991 | Thomas et al. | 24/448 |
| 5,116,563 | 5/1992 | Thomas et al. | 264/167 |
| 5,180,534 | 1/1993 | Thomas et al. | 264/145 |
| 5,221,276 | 6/1993 | Battrell | 604/391 X |
| 5,230,851 | 7/1993 | Thomas | 264/145 |
| 5,300,058 | 4/1994 | Goulait et al. | 604/391 |
| 5,308,345 | 5/1994 | Herrin | 604/385.2 |
| 5,318,741 | 6/1994 | Thomas | 264/519 |
| 5,325,569 | 7/1994 | Goulait et al. | 24/448 |
| 5,326,415 | 7/1994 | Thomas et al. | 156/244.11 |
| 5,326,612 | 7/1994 | Goulait | 428/100 |
| 5,354,591 | 10/1994 | Ott et al. | 428/99 |
| 5,383,871 | 1/1995 | Carlin et al. | 604/385.2 |
| 5,385,706 | 1/1995 | Thomas | 264/519 |
| 5,392,498 | 2/1995 | Goulait et al. | 24/452 |
| 5,447,590 | 9/1995 | Gilpatrick | 156/178 |
| 5,451,219 | 9/1995 | Suzuki et al. | 604/385.2 |
| 5,476,702 | 12/1995 | Datta et al. | 604/391 X |
| 5,540,673 | 7/1996 | Thomas et al. | 604/391 |
| 5,554,239 | 9/1996 | Datta et al. | 156/66 |
| 5,636,414 | 6/1997 | Litchholt | 24/304 |

FASTENING DEVICE AND METHOD OF USE

This application is a continuation-in-part of application Ser. No. 08/547,847, now U.S. Pat. No. 5,647,864, which is a continuation of application Ser. No. 08/254,814, filed Jun. 6, 1994, which has been abandoned.

FIELD OF THE INVENTION

The present invention relates to an improved fastening device including a combination of mechanical fastening elements and adhesive or cohesive means. The invention also relates to articles, especially disposable absorbent articles, for which the fasteners are particularly useful.

BACKGROUND OF THE INVENTION

Refastenable fastening devices of the hook and loop type are currently used in a great number of situations. Such refastenable fastening devices have been particularly useful in clothing, disposable absorbent articles, disposable diapers, disposable packages, cartons, and the like. Hook and loop type devices are often used when it is desirable to refastenably secure two or more articles or portions of an article. In certain applications, these refastenable fastening devices have replaced conventional buckles, zippers, buttons, snaps, tie fasteners, and sewing.

One popular type of mechanical fastener currently in wide use which utilizes mechanical entanglement to create a refastenable fastener is sold under the trademark "VELCRO". Some VELCRO fastening devices are described in greater detail in U.S. Pat. No. 2,717,437, U.S. Pat. No. 3,009,235, U.S. Pat. No. 3,266,113, U.S. Pat. No. 3,550,837, U.S. Pat. No. 4,169,303, and U.S. Pat. No. 4,984,339.

VELCRO fasteners generally utilize two components, a male component and a female component. The male and female components are often referred to as the hook and loop components, respectively. The male component of VELCRO-type fastening devices generally contains a plurality of resilient, upstanding hook shaped elements and the female component generally consists of a fabric containing a plurality of upstanding loops. When the male component and the loop component are pressed together in a face to face relationship to close the fastening device, the hooks entangle the loops such that the components will not easily disengage. The fastener is opened by applying a gradual peeling force to bend the resilient hooks such that they release the loops or to break the loops. In either case, it is desirable that the male and female components have enough integrity to be fastened multiple times.

SUMMARY OF THE INVENTION

The present invention is directed to a fastening system including a male component and a female component. The male component includes a base having a first fastening surface and an opposed first nonfastening surface. The first fastening surface has a plurality of engaging elements extending, each engaging element having a proximal end adjacent the first fastening surface, a stem extending outwardly from the proximal end and distal end spaced apart from the proximal end by the stem. The female component includes a backing having a second fastening surface and an opposed second nonfastening surface; and a receiving material joined to said second fastening surface. At least a portion of the second fastening surface includes a bonding element such that when the fastening system is in a closed, fastened configuration, at least a portion of the distal end of some of the engaging elements of the male component pass through the receiving material and are joined to the second fastening surface with the bonding element.

BRIEF DESCRIPTION OF THE DRAWINGS

The foregoing and other objects, features and advantages of the invention will be more apparent from the following detailed description of the invention, as illustrated in the accompanying figures of the drawings, in which like reference characters refer to the same parts throughout the different figures wherein.

DETAILED DESCRIPTION OF THE INVENTION

Overall Characteristics of the Refastenable Fastening Device

Figure 2:
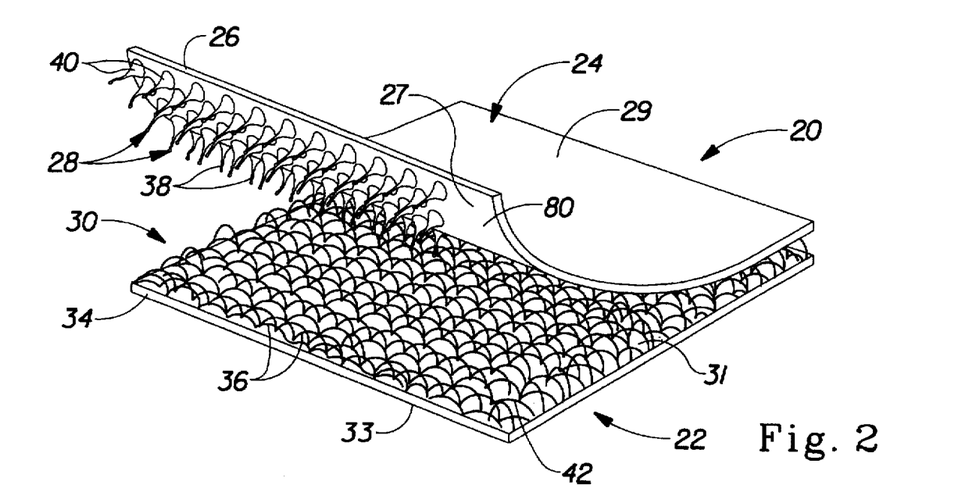
FIG. 2 is a perspective view of one embodiment of the fastening systems of the present invention.

A preferred embodiment of the refastenable fastening device of the present invention, fastening device 20, is shown in FIG. 2. The fastening device 20 comprises a female component 22 and a complementary male component 24.

The male portion of the device, more specifically, the hook fastening component (or simply "hook component") 24, preferably comprises a base 26 having a first fastening surface 27 and an opposed first nonfastening surface 29. The base 26 comprises a plurality of upstanding engaging elements 28 (such as "hooks") extending from the first surface 27. The term "hook", as used herein, is nonlimiting in the sense that the engaging elements 28 may be in any shape known in the art so long as they are adapted to engage the complimentary female component 22 of the present invention. The engaging elements 28 generally have distal ends 38 (engaging means) which are disposed on top of the shanks, or stems 40, that extend from the first fastening surface 27 of the male component 24.

Figure 3:
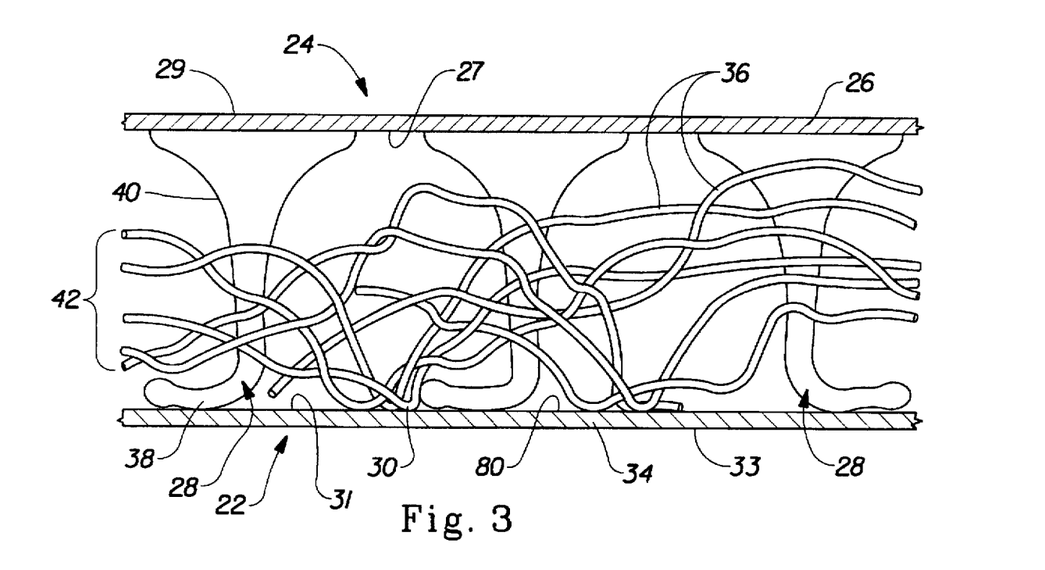
FIG. 3 is a greatly enlarged view of one embodiment of the fastening device in a closed, fastened configuration.

The female portion of the device, more specifically, the female component 22 preferably receives and entangles the engaging elements 28 of the male component 24. The female component 22, as shown in FIGS. 2 and 3, preferably comprises a receiving material 42 secured to a backing 34. The receiving material 42 preferably comprises a nonwoven web 30 including a plurality of filaments (or fibers) 36 that entangle the engaging elements 28 of the male component 24. The backing 34 has a second fastening surface 31 and a second nonfastening surface 33 opposed to the second fastening surface 31. At least a portion of the second fastening surface 31 preferably includes or is coated with bonding element 80.

A preferred embodiment of the fastening device 20 of the present invention functions in the following manner. The fastening device 20 is closed when the female component 22 and the male component 24 are pressed face-to-face against each other. In this configuration, at least some of the engaging elements 28 pass through the receiving material 42 and become joined to the bonding element 80 comprised in or disposed on the fastening surface 31 of the backing 34.

The fastening device 20 is preferably unfastened or opened by peeling the male component 24 away from the female component 22 (or by peeling the female component 22 away from the male component 24). The peeling action breaks the bond between the engaging elements 28 and the bonding element 80 of the female component 22. The engaging elements 28 no longer joined with the bonding element 80 are then able to disengage from the receiving material 42 such that the male component 24 is completely detached from the female component 22. (When hooks are used, the hooks may need to be separated from the receiving material 42 by bending the receiving material 42 or the hooks, or by breaking the receiving material 42 or the hooks.) In preferred embodiments, the fastening device 20 is capable of being refastened and reopened in the manner herein described.

The Male Fastening Component

The term "male component", as used herein, is used to designate the portion of the fastening device 20 having engaging elements 28, such as hooks or prongs. In preferred embodiments the male component 24 includes a base 26 and engaging elements 28 extending therefrom. The engaging elements 28 of the male component 24 are preferably capable of passing through the receiving material 42 of the female component 22 and becoming joined with the bonding element 80 which is associated with the backing of the female component 22.

1. The Base

In preferred embodiments, the base 26 of the male component 24 has a first fastening surface 27 and an opposed first nonfastening surface 29. When the fastening device is fastened, or closed, the first fastening surface 27 is preferable disposed toward the female component 22 and the first nonfastening surface 29 is preferably disposed away from the female component 22.

The base 26 may comprise any material known in the art which is capable of supporting the engaging elements 28 of the male component 24. For example, the base 26 may comprise a thin film having a uniform or varying thickness, slits, holes, deformations or the like, or a laminate of two or more films with any of the aforementioned characteristics. Other suitable backing materials include, but are not limited to polymeric films, foams, woven webs, nonwoven webs, apertured films, adhesives, cohesives, paper products and the like, or combinations of one or more of such materials. Further, the backing 34 may be all or any portion of the topsheet, backsheet or any other element of the article in which it is being used.

The base 26 may also be extensible, elastomeric or relatively inelastic. As used herein, the term "extensible" refers to materials that can be made longer in at least one dimension when a forces is applied. Relatively inelastic materials generally maintain their original shape under normal forces or break apart before becoming elongated. The term "elastomeric" refers to materials that extend in at least one direction when a force is applied and return to approximately their original dimensions after the force is removed. Thus, elastomeric materials have an elongated orientation (when force is applied) and a relaxed orientation (when force removed).

2. The Engaging Elements

The engaging elements 28 are that portion of the male component 24 which extend outwardly from second fastening surface 27 of the base 26. In preferred embodiments, the engaging elements 28 include a proximal end 39, a stem 40 and a distal end 38. The stem 40 extends outwardly from the proximal end 39 which is disposed adjacent the base 26. The stem 40 supports the distal end 38 of the engaging element 28 such that the distal end 38 is spaced apart from the base 26. Although there may be little or no physical distinction between the stem 40 and the distal end 38 of each engaging element 28, the distal end 38 is that portion of the engaging element 28 which generally passes through the receiving material 42 of the female component 22 and becomes joined with the bonding element 80 located in or on the second fastening surface of the backing 34.

Although the male component 24 of the present invention may have engaging elements 28 including conventional, commercially available hooks, the male component 24 is not limited to conventional hooks. In fact, suitable male components 24 may include engaging elements 28 having any shape known in the art, such as "T"s, mushrooms, prongs or any other shape which can penetrate the receiving material 42 and become joined with the bonding element 80 associated with the second fastening surface 31 of the female component 22. One preferred male component is described in U.S. Pat. No. 4,846,815 entitled "Disposable Diaper Having An Improved Fastening Device" which issued to Charles L. Scripps on Jul. 11, 1989. Other particularly preferred male components and methods for making the same are the prongs described in U.S. Pat. No. 5,058,247 entitled "Mechanical Fastening Prong" issued on Oct. 22, 1991; U.S. Pat. No. 5,116,563 entitled "Process for Producing a Mechanical Fastener" issued on May 26, 1992; U.S. Pat. No. 5,180,534 entitled "Process of Manufacturing A Refastenable Mechanical Fastening System", issued on Jan. 19, 1993; U.S. Pat. No. 5,230,851 entitled "Process of Manufacturing a Refastenable Fastening System" issued to Thomas on Jul. 27, 1993; and U.S. Pat. No. 5,540,673 entitled "Refastenable Mechanical Fastening System" issued on Jul. 30, 1996; each of which issued in the names of Thomas et al. All of the above-identified U.S. Patents are hereby incorporated by reference herein.

Figure 6:
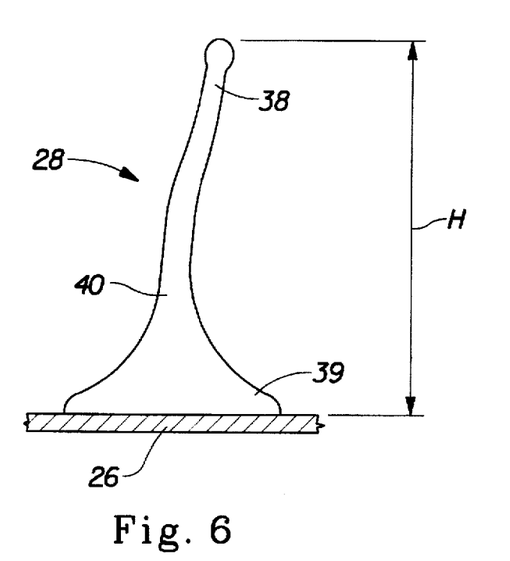
FIG. 6 is a greatly enlarged view of one embodiment of an engaging element of the present invention.

One preferred embodiment of an engaging element 28 is shown in great detail in FIG. 6. In this embodiment, the engaging element 28 is configured more like a hair than a conventional hook or "T" shaped engaging element. In such embodiments, it is preferred that the distal end 38 and the stem 40 of the engaging element 28 are thin and very flexible such that the engaging element 28 may easily bend as shown in FIG. 3. These very flexible hair-like engaging elements 28 are preferably soft to the touch and thus, provide more of a cloth-like feel than conventional hooks. Exemplary hair-like engaging elements 28 are arranged on the base 26 in any pattern, regular or irregular, with an average density of between about 400 and 3600 engaging elements 28 per square inch. Further, preferred hair-like engaging elements 28 have a height H of between about 0.1 mm and about 2 mm, more preferably between about 0.25 mm and about 1 mm, and a thickness in the stem 40 and distal ends of less than about 0.5 mm, more preferably less than about 0.2 mm.

The engaging elements 28 of the male component 24 may be manufactured is from a wide range of materials, including but not limited to thermoplastic materials, polymeric materials, adhesive materials, cohesive materials or combinations of these and other materials. Further, the engaging elements 28 may include the same or different materials than those which make up any part of the base 26. Particularly preferred materials for use in the male component 24 include nylon, polyester, polypropylene, adhesives, cohesives or any combination of these or other materials.

In embodiments wherein it is desirable for the male component 24 to include a cohesive, such as when the bonding element 80 of the female component 22 includes a cohesive, all or a part of the male component 24 may be made of or be covered with the cohesive. Likewise, the engaging elements 28 may be made from or may be covered with a cohesive or any other material which helps to attain the desired bond between the engaging elements 28 and the second fastening surface 31 of the female component 24.

The Female Fastening Component

The "female fastening component", "female component" or "landing component", which is generally designated 22 herein, is that portion of the fastening device 20 which receives and entangles the engaging elements 28 of the complementary male component 24. In one preferred embodiment, as shown in FIGS. 2 and 3, the female component 22 includes a backing 34 and a receiving material 42 joined thereto.

The female component 22 may comprise any materials or combination of materials that are known in the art. Further, the female component 22 may take on any configuration suitable for receiving the engaging members 28 of the male component 24.

1. The Backing

The backing 34 of the present invention is that part of the female fastening component 22 to which the receiving material 42 is secured. The backing 34 preferably has a second fastening surface 31 and an opposed second nonfastening surface 33. The second fastening surface 31 is preferably disposed such that it faces the male component 24 when the fastening device 20 is in a closed, fastened configuration, whereas the second nonfastening surface 33 of the backing is preferably disposed such that it faces away from the male component 24 when the fastening device 20 is fastened. The backing 34 provides a supporting foundation for is the receiving material 42.

The backing 34 of the present invention may take on a number of different configurations. For example, the backing 34 may comprise a thin film having a uniform or varying thickness, slits, holes, deformations or the like, or a laminate of two or more films with any of the aforementioned characteristics. Other suitable backing materials include, but are not limited to polymeric films, foams, woven webs, nonwoven webs, apertured films, elastomeric materials, adhesives, cohesives, paper products and the like, or combinations of one or more of such materials. The backing 34 may also be extensible, elastomeric or relatively inelastic. Further, the backing 34 may be all or any portion of the topsheet, backsheet or any other element of the article in which it is being used.

2. Bonding Member

In preferred embodiments, the female fastening component 22 includes a bonding element 80 integral with or applied to at least a portion of the first fastening surface 31 of the backing 34. (As used herein, the term "integral" refers to elements which are not discontinuous with each other, but rather, form a single structure which cannot be easily separated without generally destroying the continuous structure. An example of an integral structure would be a co-extruded film with separate elements integrally joined together.) The bonding element 80 provides a means for releasably bonding portions of the engaging elements 28 of the male component 24 with the backing 34 of the female component 22. The bonding element 80 may also provide the means by which the receiving material 42 is joined to the backing 34. In at least one embodiment, the bonding element 80 is provided on the receiving material 42 adjacent the backing 34.

Figure 1:
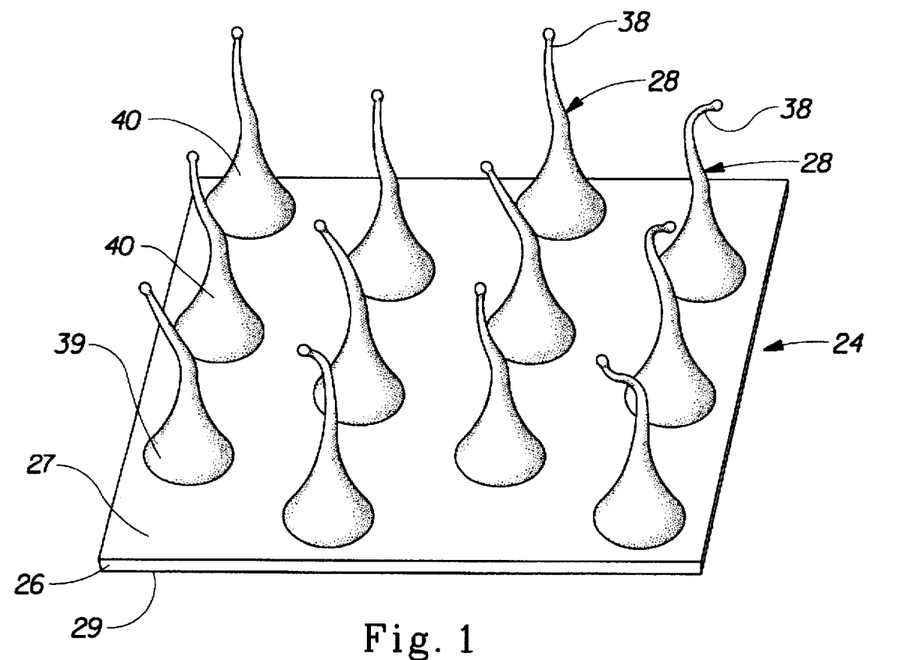
FIG. 1 is a greatly enlarged perspective view of one embodiment of a male fastening component.

The bonding element 80 provides the fastening system 20 with peel force resistance. (As used herein, "peel force resistance" is the maximum peel force in the z direction, the direction normal to the plane of the fastening mechanism, that the engaged fastener can withstand without disengaging. Peel force resistance is measured as described in U.S. Pat. No. 4,846,815 entitled "Disposable Diaper Having An Improved Fastening Device" which issued to Charles L. Scripps on Jul. 11, 1989, which is incorporated herein by reference.) The peel force resistance provided by the bonding element 80 is important when the male component 24 has engaging elements 28 which are very flexible or do not have means for securely entangling with the receiving material 42. An example would be a thin, flexible "hair" without a defined hook to entangle the filaments or other structure of the receiving material 42. Examples of such hairs are shown in FIGS. 1 and 6.) Another example of an engaging element which may perform better with the added peel force resistance associated with the bonding element is a directional engaging element which needs shear forces to keep it engaged. (Although the bonding element 80 has been described as providing peel force resistance, it should be understood that most bonding means will also provide at least some shear force resistance as well.)

The bonding element 80 may be any bonding agent or means known in the art which will releasably bond the engaging elements 28 with the first fastening surface 31 of the backing 34. (Alternative embodiments are contemplated, however, wherein the bonding element 80 provides a permanent bond.) For example, the bonding element 80 may include an adhesive, a cohesive or a combination of adhesives and/or cohesives. (The term "adhesive" refers to materials which are capable of bonding to another material by sticking, or adhering, to the surface of the other material. A "cohesive" is a material which generally only bonds to itself.) The adhesives or cohesives may be pressure sensitive, heat activated, solvent activated and/or light activated. (A "pressure sensitive adhesive" is an adhesive that is generally responsive to pressure, i.e., is capable of adhering under the influence of pressure alone.) Examples of a suitable adhesives are marketed by the Findley Adhesive Corporation of Wauwatosa, Wis. under the trade names H2206, HS2206 and 198-338. Suitable cohesives include H9078, H9054, 207-939, 211-939 and 218-939 also available from Findley Adhesive Corporation. Alternative bonding means may include static electricity, magnetism and the like.

The amount, type, and manner of applying the bonding means 80, such as those described above, can be varied to increase or decrease the shear and peel fastening characteristics of the fastening device 20. Typical adhesive and cohesive coatings are from about 0.30 mg/in$^2$ to about 1.0 g/in$^2$. Also, more bond sites or contact points between the engaging elements 28 and the adhesive, cohesive or other bonding means can increase the shear and peel force resistance.

In one preferred embodiment of a backing 34 with an integral bonding element 80, the backing 34 comprises a pressure sensitive adhesive that has been extruded in the form of a thin film of about 0.03 mm. to about 1.0 mm. (about 0.001 in. to about 0.04 in.). In other preferred embodiments however, a web of adhesive, a single or multiple strands of adhesive, discrete regions of adhesive formed in random or regular patterns or any combination of the above may be integral with or joined to the backing 34.

3. Receiving Material

The female component 22 preferably comprises a receiving material 42 to receive and entangle the engaging elements 28 of the male component 24. The receiving material 42 can be any material through which at least a portion of some of the engaging elements 28 can pass, such that they may be adhered or otherwise bonded to the second fastening surface 31 of the female component 22. When fastened in use, the receiving material 42 provides shear force resistance by preventing movement of the male fastening component 24 in the x/y plane across the surface of the female component 22. (As used herein, "shear force resistance" is defined as the force in the x/y plane that the engaged fastening mechanism can withstand without disengaging. Shear force resistance is measured as described in U.S. Pat. No. 4,699,622 entitled "Disposable Diaper Having An Improved Side Closure" issued to John W. Toussant et al. on Oct. 13, 1987, which is incorporated herein by reference.)

The receiving material 42 may comprise woven or nonwoven webs, apertured films, foams, loose fibers or any other structure extending from or joined to the second fastening surface 31 of the backing 34 having interstices through with the distal ends 38 of the engaging elements 28 may pass. Especially preferred embodiments include woven or nonwoven webs.

One example of the female fastening component 22 of the present invention having a receiving material 42 including a nonwoven web 30 is shown in FIGS. 2 and 3. Preferably portions of at least some of the filaments 36 comprised in the web 30 are joined to or extend from the second fastening surface 31 of the backing 34. The unjoined spaces between the filaments 36 of the nonwoven web 30 provide interstices through which the distal ends 38 of the engaging elements 28 can pass.

In preferred embodiments, the receiving material 42 will be chosen to have a interstices of proper size and number to allow a majority of the engaging elements 28 to pass through the receiving member 42. Thus, the size, shape and location of the interstices is important as well as the loft associated with the receiving material. (As used herein, the "loft" associated with a material is defined as the measurement taken in the "z" direction from the first fastening surface 31 of the backing 34 to the surface of the receiving material which is located away from the backing 34.) In general, the loft of the receiving material should be less than the length of the engaging elements 28 such that at least a portion of the distal ends 38 of the engaging elements 28 can reach the second fastening surface 31 of the backing 34. In some instances, the loft may be greater than the length of the engaging elements 28 until a usual force is exerted to compress the receiving material 42. An example of a common compression force which could be exerted in order to properly fasten the fastening device 20 of the present invention is between about 1 gram and about 500 grams.

In alternative embodiments, it may be desirable for the receiving material 42 to include an adhesive, cohesive or other bonding means. Such configurations may provide for better peel and/or shear resistance and may allow for reduced material usage.

Examples Of Uses Of The Refastenable Fastening Device

The refastenable fastening device 20 of the present invention is especially useful as a fastening device for absorbent and disposable absorbent articles. The term "disposable absorbent article", as used herein, refers to articles which absorb and contain body exudates. More particularly, the term refers to articles which are placed against or in proximity to the body of the wearer to absorb and contain the various exudates discharged from the body. The term "disposable" means that such articles are intended to be discarded after a single use (i.e., they are not intended to be laundered or otherwise be used). Examples of disposable absorbent articles include diapers, incontinence garments, sanitary napkins, bandages, bibs and the like.

Figure 4:
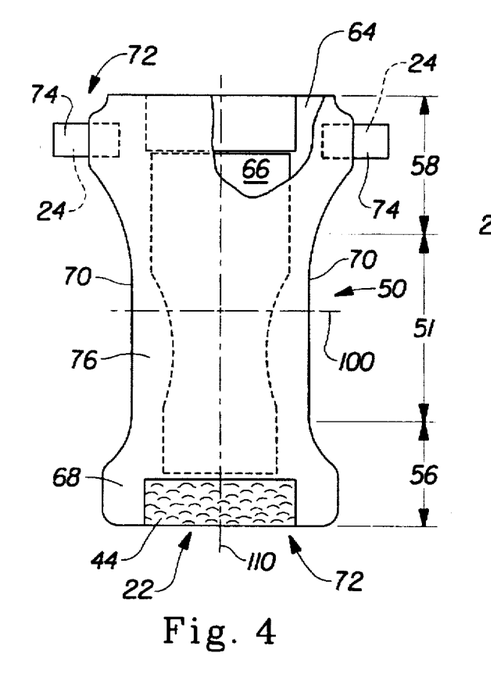
FIG. 4 is a plan view of one embodiment of a disposable absorbent garment including the fastening system of the present invention.
Figure 5:
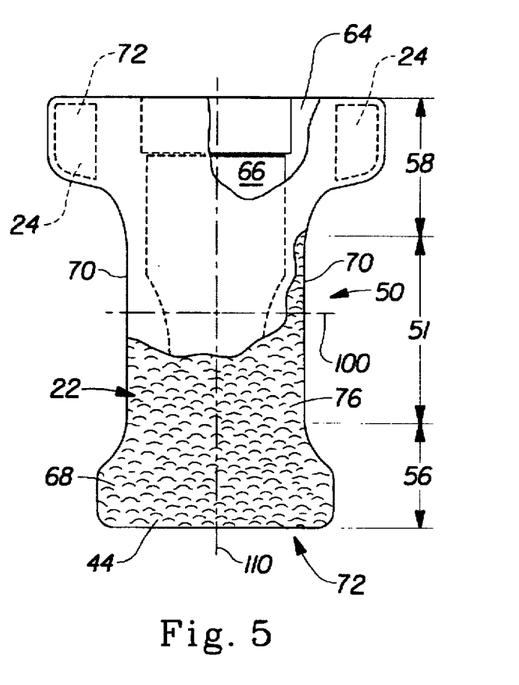
FIG. 5 is a plan view of one embodiment of the fastening system of the present invention.

FIGS. 4 and 5 show exemplary disposable diapers 50 each comprising a fastening system 72 including the female fastening component 22 of the present invention. The diaper 50 preferably comprises a crotch region 51 and two waist regions, a first waist region 56, and a second waist region 58. Preferably, at least the crotch region 51 comprises a liquid pervious topsheet 64, a liquid impervious backsheet 68, and an absorbent core 66 joined between the topsheet 64 and the backsheet 68. As used herein, the term "joined" refers to configurations whereby an element is directly secured to another element by affixing the element directly to the other element, and configurations whereby an element is indirectly secured to another element by affixing the element to intermediate member(s) which in turn are affixed to the other element.

As shown in FIGS. 4 and 5, the fastening system 72 of the diaper 50 comprises the female fastening component 22 of the present invention, among other elements. The fastening system 72 may take on a number of configurations and constructions. In one preferred embodiment, the male component 24 is disposed on a tab 74 (FIG. 4). As shown in FIG. 4, a tab 74 may be provided adjacent each longitudinal edge 70 of the diaper 50, most preferably in the second waist region 58. In such embodiments, the female component 22 is preferably disposed in at least a portion of the first waist region 56. However, the positions of the components of the fastening device 20 of the present invention could be reversed so that the male component 24 is located in the first waist region and the female component 22 is located in the second waist region.

If a tab 74 is used, any known configurations and/or constructions may be used. One preferred tape tab is a Y-shaped tape tab as described in detail in U.S. Pat. No. 3,848,594 entitled "Tape Fastening System for Disposable Diaper" which issued to Kenneth B. Buell on Nov. 19, 1974 and which patent is incorporated herein by reference.

The landing member 44 of the fastening system 72 includes the female component 22 of the present invention and provides an attachment zone for the male component 24. When the first device 72 is closed, it provides a secure side closure for the diaper 50 to maintain the first waist region 56 and the second waist region 58 in a closed, generally overlapping configuration. The landing member 44 may be disposed anywhere on the diaper 50 so long as it may be engaged by the male component 24 so as to provide the side closure. For example, the landing member 44 may be disposed on the outside surface 76 in the second waist region 58, on the inside surface 78 in the first waist region 56, or on any other portion of the diaper 50 which is disposed to engage the male component 24. In addition, the landing member 44 may be a discrete separate element affixed to an element of the diaper 50 (such as the topsheet 64 or the backsheet 68), or a unitary piece of material that is neither divided nor discontinuous with an element of the diaper 50 such as the topsheet 64 or the backsheet 68. While the landing member 44 can assume varying sizes and shapes in one preferred embodiment, it preferably comprises one or more separate patches of material that are larger in area than each male component 24 and which are secured to the diaper 50 to allow for a maximum fit adjustment in at least the waist region of the wearer. One preferred embodiment of the diaper 50, illustrated in FIG. 4, has a rectangular-shaped landing member 44 secured to the outside surface 76 of the diaper 50 in the front waist region 56.

Several examples of well known diaper configurations to which the present invention can be readily adapted are described in U.S. Pat. Nos. 5,151,092 and 5,221,274 both entitled "Absorbent Article With Dynamic Elastic Waist Feature Having A Predisposed Flexural Hinge", issued to Kenneth B. Buell, et al. on Sep. 29, 1992 and Jun. 22, 1993, respectively; co-pending U.S. patent application Ser. No. 08/155,048 entitled "Absorbent Article With Multi-Directional Extensible Side Panels", filed Nov. 19, 1993. Each of the above mentioned patents and co-pending patent applications are hereby incorporated by reference herein. It should be understood, however, that the fastening device 20 of the present invention is not limited to use with any specific diaper structure or configuration.

In another preferred embodiment, the landing member 44 of the fastening system 72, including the female component 24, is disposed across the majority of the first waist region 56 (FIG. 5). In yet other embodiments, the landing member 44 comprises most or all of the outer surface 76 of at least the first waist region 56 and the crotch region 51, and/or the second waist region 58. This provides for numerous attachment configurations and thus, better fit for a wide range of wearers.

The landing member 44 may be disposed in said second waist region 58 in order to provide greater fastening alternatives or to allow for attachment in a disposal configuration.

In use, the diaper 50 is applied to the wearer by positioning the first waist region 56 under the wearer's back and drawing the remainder of the diaper 50 between the legs of the wearer so that the second waist region 58 is positioned across the front of the wearer. The male component 24 is then placed in face-to-face relationship with the landing member 44 so at least some of the engaging elements 28 will pass through the receiving material 42 and become releasably bonded to the fastening surface 31 of the female component 22 by means of the adhesive, cohesive or other releasable bonding means.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A refastenable fastening system having an open, unfastened configuration and a closed, fastened configuration, the fastening system comprising:

a male component including a base having a first fastening surface and an opposed first nonfastening surface; said first fastening surface having a plurality of engaging elements extending therefrom; said engaging elements each having a proximal end adjacent said first fastening surface, a stem extending outwardly from said proximal end and distal end spaced apart from said proximal end by said stem; and a female component including a backing having a second fastening surface and an opposed second nonfastening surface; and a receiving material having interstices, said receiving material joined to said second fastening surface; at least a portion of said second fastening surface including a bonding element such that when the fastening system is in said closed, fastened configuration, at least a portion of said distal end of some of said engaging elements of said male component pass through said interstices of said receiving material and are joined to said second fastening surface with said bonding element.

2. The fastening system of claim 1 wherein said receiving material includes a nonwoven web.

3. The fastening system of claim 1 wherein said receiving material includes a woven web.

4. The fastening system of claim 1 wherein said receiving material includes a foam.

5. The fastening system of claim 1 wherein said receiving material includes a scrim.

6. The fastening system of claim 1 wherein said receiving material includes an apertured film.

7. The fastening system of claim 1 wherein said engaging members include hook-like elements.

8. The fastening system of claim 1 wherein said engaging members include hair-like elements.

9. The fastening system of claim 1 wherein said bonding element comprises an adhesive.

10. The fastening system of claim 1 wherein said bonding element comprises a cohesive.

11. An absorbent article having a front waist region, a rear waist region, and a crotch region located between said front waist region and said rear waist region, the absorbent article comprising;

a chassis including a topsheet, a backsheet having an inner surface and an outer surface, at least a portion of said backsheet being joined with said topsheet, and an absorbent core having a pair of opposed longitudinal edges and a pair of opposed end edges;

an ear panel having a proximal edge and a distal edge, said proximal edge disposed adjacent said longitudinal edge of said absorbent core and said distal edge extending laterally outwardly from said proximal edge;

a male component located on said ear panel, said male component including a base having a first fastening surface and an opposed first nonfastening surface; said first fastening surface having a plurality of engaging elements extending therefrom; said engaging elements each having a proximal end adjacent said first fastening surface, a stem extending outwardly from said proximal end and distal end spaced apart from said proximal end by said stem; and a female component located on said outer surface of said backsheet in at least said front waist region, said female component including a backing having a second fastening surface and an opposed second nonfastening surface; and a receiving material having interstices, said receiving material joined to said second fastening surface; at least a portion of said second fastening surface including a bonding element such that when the fastening system is in a closed, fastened configuration, at least a portion of said distal end of some of said engaging elements of said male component pass through said interstices of said receiving material and are respectively joined to said second fastening surface with said bonding element.

12. The absorbent article of claim 11 wherein said female component includes a discrete patch joined with said outer surface of said backsheet in at least said front waist region.

13. The absorbent article of claim 11 wherein said female component is integral with said backsheet.

14. The absorbent article of claim 11 wherein said female component is disposed in at least a portion of said front waist region and at least a portion of said rear waist region to provide a means for disposal.

15. The absorbent article of claim 11 wherein said receiving material is selected from the following group: apertured film, nonwoven web, foam and scrim.

16. The absorbent article of claim 11 wherein said engaging members include hook-like elements.

17. The absorbent article of claim 11 wherein said bonding element comprises an adhesive.

18. The absorbent article of claim 11 wherein said bonding element comprises a cohesive.

19. The absorbent article of claim 11 wherein said engaging members include hair-like elements.

20. A method of fastening a fastening device having a male component and a female component, the method comprising the steps of a) providing a male fastening component including
  i) a base having a first fastening surface and a first nonfastening surface, and
  ii) at least one engaging element extending from said base, said engaging element including a proximal end adjacent said first fastening surface of said base, a stem extending outwardly from said proximal end and a distal end spaced apart from said proximal end by said stem;

(b) providing a female fastening component including
  (i) a backing having a second fastening surface and a second nonfastening surface, said second fastening surface including a bonding element; and
  (ii) a receiving material having interstices, said receiving material engageable with said male component joined with said second fastening surface of said backing;

(c) contacting said male fastening component to said female fastening component such that the distal ends of at least some of said engaging elements pass through said interstices of said receiving material and become releasably joined with said bonding element of said female fastening component.

* * * * *

UNITED STATES PATENT AND TRADEMARK OFFICE
CERTIFICATE OF CORRECTION

| | | |
|---|---|---|
| PATENT NO. | : 5,762,645 | Page 1 of 1 |
| DATED | : June 9, 1998 | |
| INVENTOR(S) | : Daniel C. Peck et al. | |

It is certified that error appears in the above-identified patent and that said Letters Patent is hereby corrected as shown below:

Column 10,
Line 61, "respectively" should read -- releasably --.

Signed and Sealed this

Eleventh Day of December, 2001

Attest:

*Attesting Officer*

NICHOLAS P. GODICI
*Acting Director of the United States Patent and Trademark Office*